United States Patent
Schreck

(10) Patent No.: US 9,393,100 B2
(45) Date of Patent: Jul. 19, 2016

(54) DEVICES AND METHODS TO TREAT VASCULAR DISSECTIONS

(75) Inventor: Stefan G. Schreck, Fallbrook, CA (US)

(73) Assignee: Endologix, Inc., Irvine, CA (US)

( * ) Notice: Subject to any disclaimer, the term of this patent is extended or adjusted under 35 U.S.C. 154(b) by 452 days.

(21) Appl. No.: 13/988,175

(22) PCT Filed: Nov. 16, 2011

(86) PCT No.: PCT/US2011/061061
§ 371 (c)(1),
(2), (4) Date: May 17, 2013

(87) PCT Pub. No.: WO2012/068298
PCT Pub. Date: May 24, 2012

(65) Prior Publication Data
US 2013/0253632 A1    Sep. 26, 2013

Related U.S. Application Data

(60) Provisional application No. 61/414,819, filed on Nov. 17, 2010.

(51) Int. Cl.
*A61F 2/06* (2013.01)
*A61F 2/82* (2013.01)
*A61M 25/00* (2006.01)
*A61M 25/01* (2006.01)

(52) U.S. Cl.
CPC ... *A61F 2/06* (2013.01); *A61F 2/82* (2013.01); *A61M 25/0043* (2013.01); *A61M 25/01* (2013.01)

(58) Field of Classification Search
CPC ........ A61F 2/06; A61F 2/82; A61M 25/0043; A61M 25/01
See application file for complete search history.

(56) References Cited

U.S. PATENT DOCUMENTS

| | | | |
|---|---|---|---|
| 2,127,903 A | 8/1938 | Bowen |
| 2,437,542 A | 5/1944 | Krippendorf |
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,805,301 A | 4/1974 | Liebig |
| 3,996,938 A | 12/1976 | Clark, III |
| 4,362,156 A | 12/1982 | Feller, Jr. et al. |
| 4,473,067 A | 9/1984 | Schiff |
| 4,497,074 A | 2/1985 | Ray et al. |

(Continued)

FOREIGN PATENT DOCUMENTS

| | | |
|---|---|---|
| CA | 2220141 | 11/1996 |
| CA | 2133530 | 1/1999 |

(Continued)

OTHER PUBLICATIONS

Carmi et al., "Endovascular stent-graft adapted to the endoluminal environment: prototype of a new endoluminal approach," J Endovasc Ther. Jun. 2002;9(3):380-381.

(Continued)

*Primary Examiner* — Amy R Weisberg
(74) *Attorney, Agent, or Firm* — Knobbe Martens Olson & Bear LLP

(57) ABSTRACT

A device system and method for the treatment of aortic dissections comprising placing a stent in the true lumen and displacing the blood in the false lumen with an inflatable bag.

12 Claims, 9 Drawing Sheets

(56) References Cited

U.S. PATENT DOCUMENTS

| | | |
|---|---|---|
| 4,501,263 A | 2/1985 | Harbuck |
| 4,503,568 A | 3/1985 | Madras |
| 4,525,157 A | 6/1985 | Vaillancourt |
| 4,562,596 A | 1/1986 | Kornberg |
| 4,580,568 A | 4/1986 | Gianturco |
| 4,592,754 A | 6/1986 | Gupte et al. |
| 4,617,932 A | 10/1986 | Kornberg |
| 4,638,803 A | 1/1987 | Rand |
| 4,641,653 A | 2/1987 | Rockey |
| 4,650,466 A | 3/1987 | Luther |
| 4,728,328 A | 3/1988 | Hughes et al. |
| 4,756,307 A | 7/1988 | Crownshield |
| 4,800,882 A | 1/1989 | Gianturco |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,981,478 A | 1/1991 | Evard et al. |
| 4,981,947 A | 1/1991 | Tomagou et al. |
| 4,994,069 A | 2/1991 | Ritchrt et al. |
| 4,994,071 A | 2/1991 | MacGregor |
| 4,998,539 A | 3/1991 | Delsanti |
| 5,015,232 A | 5/1991 | Maglinte |
| 5,019,090 A | 5/1991 | Pinchuk |
| 5,034,001 A | 7/1991 | Garrison et al. |
| 5,035,706 A | 7/1991 | Giantureo et al. |
| 5,041,093 A | 8/1991 | Chu |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,116,349 A | 5/1992 | Aranyi |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,145,620 A | 9/1992 | Sakai et al. |
| 5,147,334 A | 9/1992 | Moss |
| 5,156,619 A | 10/1992 | Ehrenfeld |
| 5,156,620 A | 10/1992 | Pigott |
| 5,178,634 A | 1/1993 | Martinez |
| 5,197,976 A | 3/1993 | Herweck et al. |
| 5,201,757 A | 4/1993 | Heyn et al. |
| 5,211,658 A | 5/1993 | Clouse |
| 5,256,141 A | 10/1993 | Gencheff et al. |
| 5,275,622 A | 1/1994 | Lazarus et al. |
| 5,282,824 A | 2/1994 | Gianturco |
| 5,282,860 A | 2/1994 | Matsuno et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpiel |
| 5,330,500 A | 7/1994 | Song |
| 5,330,528 A | 7/1994 | Laxim |
| 5,338,298 A | 8/1994 | McIntyre |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,370,691 A | 12/1994 | Samson |
| 5,387,235 A | 2/1995 | Chuter |
| 5,397,355 A | 3/1995 | Marin et al. |
| 5,405,377 A | 4/1995 | Cragg |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |
| 5,443,500 A | 8/1995 | Sigwart |
| 5,449,372 A | 9/1995 | Schmaltz et al. |
| 5,458,575 A | 10/1995 | Wang |
| 5,458,615 A | 10/1995 | Klemm et al. |
| 5,462,530 A | 10/1995 | Jang |
| 5,464,419 A | 11/1995 | Glastra |
| 5,464,450 A | 11/1995 | Buscemi et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,769 A | 4/1996 | Marin et al. |
| 5,507,770 A | 4/1996 | Turk |
| 5,507,771 A | 4/1996 | Gianturco |
| 5,514,379 A * | 5/1996 | Weissleder ........... A61K 9/1658 424/426 |
| 5,522,880 A | 6/1996 | Barone et al. |
| 5,522,881 A | 6/1996 | Lentz |
| 5,522,883 A | 6/1996 | Slater et al. |
| 5,529,653 A | 6/1996 | Glastra |
| 5,530,528 A | 6/1996 | Houki et al. |
| 5,534,024 A | 7/1996 | Rogers et al. |
| 5,545,211 A | 8/1996 | An et al. |
| 5,554,118 A | 9/1996 | Jang |
| 5,554,181 A | 9/1996 | Das |
| 5,562,697 A | 10/1996 | Christiansen |
| 5,562,726 A | 10/1996 | Chuter |
| 5,562,727 A | 10/1996 | Turk et al. |
| 5,562,728 A | 10/1996 | Lazarus et al. |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,197 A | 1/1997 | Orth et al. |
| 5,591,198 A | 1/1997 | Boyle et al. |
| 5,591,199 A | 1/1997 | Porter et al. |
| 5,591,229 A | 1/1997 | Parodi |
| 5,591,230 A | 1/1997 | Horn et al. |
| 5,593,417 A | 1/1997 | Rhodes |
| 5,604,435 A | 2/1997 | Foo et al. |
| 5,607,445 A | 3/1997 | Summers |
| 5,607,468 A | 3/1997 | Rogers et al. |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |

(56) References Cited

U.S. PATENT DOCUMENTS

| | | |
|---|---|---|
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,697,968 A | 12/1997 | Rogers et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,725,535 A | 3/1998 | Hegde et al. |
| 5,733,325 A | 3/1998 | Robinson et al. |
| 5,746,776 A | 5/1998 | Smith et al. |
| 5,749,880 A | 5/1998 | Banas et al. |
| 5,752,974 A | 5/1998 | Rhee et al. |
| 5,755,770 A | 5/1998 | Ravenscroft |
| 5,755,771 A | 5/1998 | Penn et al. |
| 5,755,777 A | 5/1998 | Chuter |
| 5,766,204 A | 6/1998 | Porter et al. |
| 5,769,882 A | 6/1998 | Fogarty et al. |
| 5,769,885 A | 6/1998 | Quiachon et al. |
| 5,769,887 A | 6/1998 | Brown et al. |
| 5,782,855 A | 7/1998 | Lau et al. |
| 5,782,909 A | 7/1998 | Quiachon et al. |
| 5,785,679 A | 7/1998 | Abolfathi et al. |
| 5,800,407 A | 9/1998 | Eldor |
| 5,800,456 A | 9/1998 | Maeda et al. |
| 5,800,508 A | 9/1998 | Goicoechea et al. |
| 5,800,526 A | 9/1998 | Anderson et al. |
| 5,810,836 A | 9/1998 | Hussein et al. |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,846,261 A | 12/1998 | Kotula et al. |
| 5,851,228 A | 12/1998 | Pinheiro |
| 5,855,565 A | 1/1999 | Bar-Cohen et al. |
| 5,855,599 A | 1/1999 | Wan |
| 5,860,998 A | 1/1999 | Robinson et al. |
| 5,867,432 A | 2/1999 | Toda |
| 5,868,783 A | 2/1999 | Tower |
| 5,871,536 A | 2/1999 | Lazarus |
| 5,871,537 A | 2/1999 | Holman et al. |
| 5,874,500 A | 2/1999 | Rhee et al. |
| 5,876,448 A | 3/1999 | Thompson et al. |
| 5,879,321 A | 3/1999 | Hill |
| 5,879,366 A | 3/1999 | Shau et al. |
| 5,891,193 A | 4/1999 | Robinson et al. |
| 5,893,887 A | 4/1999 | Jayaraman |
| 5,902,334 A | 5/1999 | Dwyer et al. |
| 5,906,640 A | 5/1999 | Penn et al. |
| 5,906,641 A | 5/1999 | Thompson et al. |
| 5,916,263 A | 6/1999 | Goicoceha et al. |
| 5,919,225 A | 7/1999 | Lau et al. |
| 5,921,954 A * | 7/1999 | Mohr, Jr. ............ A61B 18/1492 604/508 |
| 5,925,075 A | 7/1999 | Myers et al. |
| 5,928,279 A | 7/1999 | Shannon et al. |
| 5,931,866 A | 8/1999 | Frantzen |
| 5,935,161 A | 8/1999 | Robinson et al. |
| 5,938,696 A | 8/1999 | Goicoechea et al. |
| 5,948,018 A | 9/1999 | Dereume et al. |
| 5,957,901 A | 9/1999 | Mottola et al. |
| 5,957,973 A | 9/1999 | Quiachon et al. |
| 5,961,546 A | 10/1999 | Robinson et al. |
| 5,961,548 A | 10/1999 | Shmulewitz |
| 5,994,750 A | 11/1999 | Yagi |
| 6,001,125 A | 12/1999 | Golds et al. |
| 6,004,347 A | 12/1999 | McNamara et al. |
| 6,004,348 A | 12/1999 | Banas et al. |
| 6,007,575 A | 12/1999 | Samuels |
| 6,015,431 A | 1/2000 | Thornton et al. |
| 6,017,363 A | 1/2000 | Hojeibane |
| 6,022,359 A | 2/2000 | Frantzen |
| 6,027,779 A | 2/2000 | Campbell et al. |
| 6,027,811 A | 2/2000 | Campbell et al. |
| 6,030,415 A | 2/2000 | Chuter |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,932 A | 4/2000 | Daniel et al. |
| 6,053,940 A | 4/2000 | Wijay |
| 6,059,823 A | 5/2000 | Holman et al. |
| 6,063,113 A | 5/2000 | Kavteladze et al. |
| 6,070,589 A | 6/2000 | Keith et al. |
| 6,074,398 A | 6/2000 | Leschinsky |
| 6,077,296 A | 6/2000 | Shokoohi et al. |
| 6,077,297 A | 6/2000 | Robinson et al. |
| 6,083,259 A | 7/2000 | Frantzen |
| 6,086,611 A | 7/2000 | Duffy et al. |
| 6,090,128 A | 7/2000 | Douglas |
| 6,093,203 A | 7/2000 | Uflacker |
| 6,096,021 A * | 8/2000 | Helm ............... A61B 17/12113 604/103.01 |
| 6,096,053 A | 8/2000 | Bates |
| 6,106,548 A | 8/2000 | Reubin et al. |
| 6,110,198 A | 8/2000 | Fogarty et al. |
| 6,117,167 A | 9/2000 | Goicoechea et al. |
| 6,123,715 A | 9/2000 | Amplatz |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,139,573 A | 10/2000 | Sogard et al. |
| 6,168,592 B1 | 1/2001 | Kupiecki et al. |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,034 B1 | 2/2001 | Frantzen |
| 6,187,036 B1 | 2/2001 | Shaolian |
| 6,190,402 B1 | 2/2001 | Horton et al. |
| 6,192,944 B1 | 2/2001 | Greenhalgh |
| 6,193,745 B1 | 2/2001 | Fogarty et al. |
| 6,196,230 B1 | 3/2001 | Hall et al. |
| 6,197,049 B1 | 3/2001 | Shaolian et al. |
| 6,203,735 B1 | 3/2001 | Edwin et al. |
| 6,214,022 B1 | 4/2001 | Taylor et al. |
| 6,221,102 B1 | 4/2001 | Baker et al. |
| 6,231,562 B1 | 5/2001 | Khosravi et al. |
| 6,231,563 B1 | 5/2001 | White et al. |
| 6,235,050 B1 | 5/2001 | Quiachon et al. |
| 6,245,099 B1 | 6/2001 | Edwin et al. |
| 6,261,305 B1 | 7/2001 | Marotta et al. |
| 6,261,316 B1 | 7/2001 | Shaolian et al. |
| 6,267,775 B1 | 7/2001 | Clerc et al. |
| 6,273,909 B1 | 8/2001 | Kugler et al. |
| 6,280,466 B1 | 8/2001 | Kugler et al. |
| 6,280,467 B1 | 8/2001 | Leonhardt |

(56) References Cited

U.S. PATENT DOCUMENTS

| | | |
|---|---|---|
| 6,283,991 B1 | 9/2001 | Cox et al. |
| 6,293,969 B1 | 9/2001 | Chuter |
| 6,296,603 B1 | 10/2001 | Turnlund et al. |
| 6,299,597 B1 | 10/2001 | Buscemi et al. |
| 6,312,407 B1 | 11/2001 | Zadno-Azizi et al. |
| 6,312,462 B1 | 11/2001 | McDermott et al. |
| 6,312,463 B1 | 11/2001 | Rourke et al. |
| 6,319,276 B1 | 11/2001 | Holman et al. |
| 6,331,184 B1 | 12/2001 | Abrams |
| 6,334,869 B1 | 1/2002 | Leonhardt et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,557 B1 | 3/2002 | Gittings et al. |
| 6,361,637 B2 | 3/2002 | Martin et al. |
| 6,375,666 B1 | 4/2002 | Mische |
| 6,383,214 B1 | 5/2002 | Banas et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,413,273 B1 | 7/2002 | Baum et al. |
| 6,416,474 B1 | 7/2002 | Penner et al. |
| 6,416,542 B1 | 7/2002 | Marcade et al. |
| 6,432,131 B1 | 8/2002 | Ravenscroft |
| 6,432,134 B1 | 8/2002 | Anson et al. |
| 6,463,317 B1 | 10/2002 | Kucharczyk et al. |
| 6,464,721 B1 | 10/2002 | Marcade et al. |
| 6,475,166 B1 | 11/2002 | Escano |
| 6,475,170 B1 | 11/2002 | Doron et al. |
| 6,491,719 B1 | 12/2002 | Fogrty et al. |
| 6,500,202 B1 | 12/2002 | Shaolian et al. |
| 6,506,204 B2 | 1/2003 | Mazzocchi |
| 6,508,833 B2 | 1/2003 | Pavcnik et al. |
| 6,508,835 B1 | 1/2003 | Shaolian et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,763 B1 | 3/2003 | Schneiter |
| 6,533,811 B1 | 3/2003 | Ryan et al. |
| 6,544,276 B1 | 4/2003 | Azizi |
| 6,551,350 B1 | 4/2003 | Thornton et al. |
| 6,558,396 B1 | 5/2003 | Inoue |
| 6,558,414 B2 | 5/2003 | Layne |
| 6,562,063 B1 | 5/2003 | Euteneuer et al. |
| 6,565,596 B1 | 5/2003 | White et al. |
| 6,565,597 B1 | 5/2003 | Fearnot et al. |
| RE38,146 E | 6/2003 | Palmaz et al. |
| 6,572,645 B2 | 6/2003 | Leonhardt |
| 6,572,648 B1 * | 6/2003 | Klumb ............... A61F 2/88 623/1.15 |
| 6,575,994 B1 | 6/2003 | Marin et al. |
| 6,576,009 B2 | 6/2003 | Ryan et al. |
| 6,582,460 B1 | 6/2003 | Cryer |
| 6,585,758 B1 | 7/2003 | Chouinard et al. |
| 6,592,614 B2 | 7/2003 | Lenker et al. |
| 6,592,615 B1 | 7/2003 | Marcade et al. |
| 6,610,087 B1 | 8/2003 | Zarbatany et al. |
| 6,613,037 B2 | 9/2003 | Khosravi et al. |
| 6,613,073 B1 | 9/2003 | White et al. |
| 6,614,026 B1 | 9/2003 | Adamec |
| 6,616,675 B1 | 9/2003 | Evard et al. |
| 6,626,939 B1 | 9/2003 | Burnside et al. |
| 6,652,579 B1 | 11/2003 | Cox et al. |
| 6,656,214 B1 | 12/2003 | Fogarty et al. |
| 6,663,607 B2 | 12/2003 | Slaikeu et al. |
| 6,663,667 B2 | 12/2003 | Dehdashtian et al. |
| 6,669,718 B2 | 12/2003 | Besselink |
| 6,673,042 B1 | 1/2004 | Samson et al. |
| 6,673,105 B1 | 1/2004 | Chen |
| 6,692,512 B2 | 2/2004 | Jang |
| 6,692,523 B2 | 2/2004 | Holman et al. |
| 6,695,833 B1 | 2/2004 | Frantzen |
| 6,695,875 B2 * | 2/2004 | Stelter ............... A61F 2/07 623/1.13 |
| 6,699,276 B2 | 3/2004 | Sogard et al. |
| 6,706,064 B1 | 3/2004 | Anson |
| 6,729,356 B1 | 5/2004 | Baker et al. |
| 6,730,119 B1 | 5/2004 | Smalling |
| 6,733,523 B2 | 5/2004 | Shaolian et al. |
| 6,748,953 B2 | 6/2004 | Sherry et al. |
| 6,756,007 B2 | 6/2004 | Pletzer et al. |
| 6,761,733 B2 | 7/2004 | Chobotov et al. |
| 6,767,359 B2 | 7/2004 | Weadock |
| 6,818,014 B2 | 11/2004 | Brown et al. |
| 6,821,292 B2 | 11/2004 | Pazienza et al. |
| 6,827,735 B2 | 12/2004 | Greenberg |
| 6,843,803 B2 | 1/2005 | Ryan et al. |
| 6,899,728 B1 | 5/2005 | Phillips et al. |
| 6,918,926 B2 | 7/2005 | Letort |
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,953,475 B2 | 10/2005 | Shaolian et al. |
| 6,960,217 B2 | 11/2005 | Bolduc |
| 6,960,227 B2 | 11/2005 | Jones et al. |
| 6,981,982 B2 | 1/2006 | Armstrong et al. |
| 6,984,244 B2 | 1/2006 | Perez et al. |
| 6,994,722 B2 | 2/2006 | DiCarlo |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,494 B2 | 4/2006 | Soun et al. |
| 7,029,496 B2 | 4/2006 | Rakos et al. |
| 7,033,389 B2 | 4/2006 | Sherry |
| 7,063,707 B2 | 6/2006 | Bose et al. |
| 7,074,213 B2 | 7/2006 | McGuckin, Jr. et al. |
| 7,074,236 B2 | 7/2006 | Rabkin et al. |
| 7,081,129 B2 | 7/2006 | Chobotov |
| 7,108,715 B2 | 9/2006 | Lawrence-Brown et al. |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,160,318 B2 | 1/2007 | Greenberg et al. |
| 7,163,715 B1 | 1/2007 | Kramer |
| 7,175,652 B2 | 2/2007 | Cook et al. |
| 7,175,657 B2 | 2/2007 | Khan et al. |
| 7,189,256 B2 | 3/2007 | Smith |
| 7,192,441 B2 | 3/2007 | Sherry |
| 7,201,770 B2 | 4/2007 | Johnson et al. |
| 7,217,255 B2 | 5/2007 | Boyle et al. |
| 7,235,095 B2 | 6/2007 | Haverkost et al. |
| 7,241,308 B2 | 7/2007 | Andreas et al. |
| 7,244,444 B2 | 7/2007 | Bates |
| 7,255,711 B2 | 8/2007 | Holman et al. |
| 7,261,733 B1 | 8/2007 | Brown et al. |
| 7,264,631 B2 | 9/2007 | DiCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,314,483 B2 | 1/2008 | Landau et al. |
| 7,320,703 B2 | 1/2008 | DiMatteo et al. |
| 7,331,980 B2 | 2/2008 | Dubrul et al. |
| 7,402,168 B2 | 7/2008 | Acosta et al. |
| 7,435,253 B1 | 10/2008 | Hartley et al. |
| 7,481,822 B1 | 1/2009 | Baker et al. |
| 7,491,230 B2 | 2/2009 | Holman et al. |
| 7,520,895 B2 | 4/2009 | Douglas et al. |
| 7,530,988 B2 | 5/2009 | Evans et al. |
| 7,553,324 B2 | 6/2009 | Andreas et al. |

(56) References Cited

U.S. PATENT DOCUMENTS

| | | |
|---|---|---|
| 7,572,289 B2 | 8/2009 | Sisken et al. |
| 7,588,825 B2 | 9/2009 | Bell et al. |
| 7,637,932 B2 | 12/2009 | Bolduc et al. |
| 7,651,519 B2 | 1/2010 | Dittman |
| 7,666,220 B2 | 2/2010 | Evans et al. |
| 7,666,333 B2 | 2/2010 | Lanphere et al. |
| 7,674,284 B2 | 3/2010 | Melsheimer |
| 7,682,383 B2 | 3/2010 | Robin |
| 7,691,135 B2 | 4/2010 | Shaolian et al. |
| 7,722,657 B2 | 5/2010 | Hartley |
| 7,766,959 B2 | 8/2010 | DiMatteo et al. |
| 7,776,063 B2 | 8/2010 | Sawhney et al. |
| 7,785,365 B2 | 8/2010 | Holman et al. |
| 7,790,273 B2 | 9/2010 | Lee et al. |
| 7,833,259 B2 | 11/2010 | Boatman |
| 7,879,081 B2 | 2/2011 | DiMatteo et al. |
| 2001/0020184 A1 | 9/2001 | Dehdashtian et al. |
| 2001/0044647 A1 | 11/2001 | Pinchuk et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0049412 A1 | 4/2002 | Madrid et al. |
| 2002/0052643 A1 | 5/2002 | Wholey et al. |
| 2002/0082620 A1* | 6/2002 | Lee ................ A61B 17/00491 606/151 |
| 2002/0143348 A1* | 10/2002 | Wallace ........... A61B 17/12022 606/157 |
| 2002/0165521 A1 | 11/2002 | Cioanta et al. |
| 2002/0169497 A1 | 11/2002 | Wholey et al. |
| 2003/0004560 A1 | 1/2003 | Chobotov et al. |
| 2003/0009132 A1 | 1/2003 | Schwartz et al. |
| 2003/0014075 A1* | 1/2003 | Rosenbluth ...... A61B 17/12022 606/213 |
| 2003/0036745 A1 | 2/2003 | Khosravi et al. |
| 2003/0051735 A1 | 3/2003 | Pavcnik et al. |
| 2003/0097169 A1 | 5/2003 | Brucker et al. |
| 2003/0130725 A1 | 7/2003 | DePalma et al. |
| 2003/0135269 A1 | 7/2003 | Swanstrom |
| 2003/0163192 A1* | 8/2003 | Wallace ........... A61B 17/12109 623/1.11 |
| 2003/0204242 A1 | 10/2003 | Zarins et al. |
| 2003/0204249 A1 | 10/2003 | Letort |
| 2003/0208257 A1 | 11/2003 | Holman et al. |
| 2003/0216802 A1 | 11/2003 | Chobotov et al. |
| 2003/0220684 A1 | 11/2003 | Holman et al. |
| 2003/0225453 A1 | 12/2003 | Murch |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0098096 A1 | 5/2004 | Eton |
| 2004/0116997 A1 | 6/2004 | Taylor et al. |
| 2004/0167597 A1 | 8/2004 | Costantino et al. |
| 2004/0167607 A1 | 8/2004 | Frantzen |
| 2004/0167618 A1 | 8/2004 | Shaolian et al. |
| 2004/0176832 A1 | 9/2004 | Hartley et al. |
| 2004/0193245 A1 | 9/2004 | Deem et al. |
| 2004/0204755 A1 | 10/2004 | Robin |
| 2004/0215316 A1 | 10/2004 | Smalling |
| 2004/0220522 A1 | 11/2004 | Briscoe et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0038494 A1 | 2/2005 | Eidenschink |
| 2005/0058327 A1 | 3/2005 | Pieper |
| 2005/0059994 A1 | 3/2005 | Walak et al. |
| 2005/0060025 A1 | 3/2005 | Mackiewicz et al. |
| 2005/0065592 A1 | 3/2005 | Holzer |
| 2005/0080476 A1 | 4/2005 | Gunderson et al. |
| 2005/0090804 A1 | 4/2005 | Chobotov et al. |
| 2005/0107817 A1 | 5/2005 | White et al. |
| 2005/0113693 A1 | 5/2005 | Smith et al. |
| 2005/0113905 A1 | 5/2005 | Greenberg et al. |
| 2005/0119731 A1 | 6/2005 | Brucker et al. |
| 2005/0121120 A1 | 6/2005 | Van Dijk et al. |
| 2005/0155608 A1 | 7/2005 | Pavcnik et al. |
| 2005/0158272 A1 | 7/2005 | Whirley et al. |
| 2005/0159803 A1 | 7/2005 | Lad et al. |
| 2005/0165480 A1 | 7/2005 | Jordan et al. |
| 2005/0171593 A1 | 8/2005 | Whirley et al. |
| 2005/0171598 A1 | 8/2005 | Schaeffer |
| 2005/0215989 A1 | 9/2005 | Abboud et al. |
| 2005/0216047 A1 | 9/2005 | Kumoyama et al. |
| 2005/0240153 A1 | 10/2005 | Opie |
| 2005/0240258 A1 | 10/2005 | Bolduc et al. |
| 2005/0240260 A1 | 10/2005 | Bolduc |
| 2005/0245891 A1* | 11/2005 | McCormick ...... A61B 17/12022 604/507 |
| 2005/0251251 A1 | 11/2005 | Cribier |
| 2005/0271727 A1 | 12/2005 | Yao |
| 2006/0025853 A1* | 2/2006 | Evans ....................... A61F 2/07 623/1.21 |
| 2006/0030911 A1 | 2/2006 | Letort |
| 2006/0074481 A1 | 4/2006 | Vardi et al. |
| 2006/0142836 A1* | 6/2006 | Hartley ..................... A61F 2/07 623/1.11 |
| 2006/0161247 A1 | 7/2006 | Sherry |
| 2006/0167538 A1 | 7/2006 | Rucker |
| 2006/0200184 A1 | 9/2006 | Deal |
| 2006/0210635 A1 | 9/2006 | Laurent et al. |
| 2006/0212112 A1 | 9/2006 | Evans et al. |
| 2006/0217796 A1 | 9/2006 | DiMatteo et al. |
| 2006/0233990 A1 | 10/2006 | Humphrey et al. |
| 2006/0233991 A1 | 10/2006 | Humphrey et al. |
| 2006/0259122 A1* | 11/2006 | Eliseev ................ A01H 4/001 623/1.12 |
| 2006/0276881 A1 | 12/2006 | Holman et al. |
| 2006/0292206 A1* | 12/2006 | Kim ................ A61B 17/12022 424/443 |
| 2007/0016243 A1 | 1/2007 | Ramaiah et al. |
| 2007/0027467 A1 | 2/2007 | Ortiz et al. |
| 2007/0050008 A1 | 3/2007 | Kim et al. |
| 2007/0055355 A1* | 3/2007 | Kim ................ A61B 17/12022 623/1.21 |
| 2007/0061005 A1 | 3/2007 | Kim et al. |
| 2007/0078506 A1* | 4/2007 | McCormick ............... A61F 2/07 623/1.11 |
| 2007/0142817 A1 | 6/2007 | Hurt |
| 2007/0148128 A1 | 6/2007 | Kennedy et al. |
| 2007/0150041 A1* | 6/2007 | Evans ............... A61B 17/12118 623/1.11 |
| 2007/0162106 A1 | 7/2007 | Evans et al. |
| 2007/0203571 A1 | 8/2007 | Kaplan et al. |
| 2007/0208367 A1 | 9/2007 | Fiorella et al. |
| 2007/0213804 A1 | 9/2007 | Kaplan et al. |
| 2007/0276477 A1 | 11/2007 | Lee et al. |
| 2007/0282424 A1 | 12/2007 | Holman et al. |
| 2008/0009936 A1 | 1/2008 | Kim et al. |
| 2008/0039923 A1 | 2/2008 | Taylor et al. |
| 2008/0071298 A1 | 3/2008 | Khairkhahan et al. |
| 2008/0109055 A1* | 5/2008 | Hlavka ..................... A61F 2/95 623/1.1 |
| 2008/0114440 A1* | 5/2008 | Hlavka ..................... A61F 2/95 623/1.12 |
| 2008/0132936 A1 | 6/2008 | Sawhney et al. |
| 2008/0215087 A1 | 9/2008 | Pavcnik et al. |
| 2008/0228259 A1* | 9/2008 | Chu ....................... A61F 2/07 623/1.11 |
| 2008/0275536 A1 | 11/2008 | Zarins et al. |
| 2008/0300672 A1 | 12/2008 | Kassab et al. |
| 2009/0068279 A1 | 3/2009 | Richard |
| 2009/0081275 A1 | 3/2009 | Rolfes et al. |
| 2009/0105805 A1 | 4/2009 | Baker et al. |
| 2009/0112302 A1* | 4/2009 | Stafford ............... A61B 17/064 623/1.11 |
| 2009/0125053 A1* | 5/2009 | Ferrera ............. A61B 17/1214 606/200 |
| 2009/0198267 A1 | 8/2009 | Evans et al. |
| 2009/0222078 A1* | 9/2009 | Greenberg .................. A61F 2/07 623/1.13 |
| 2009/0264993 A1* | 10/2009 | Greenan ..................... A61F 2/07 623/1.36 |
| 2009/0270965 A1* | 10/2009 | Sinha ..................... A61F 2/07 623/1.11 |
| 2009/0287145 A1 | 11/2009 | Cragg et al. |

(56) References Cited

U.S. PATENT DOCUMENTS

| | | | |
|---|---|---|---|
| 2009/0306763 A1* | 12/2009 | Roeder | A61F 2/07 623/1.13 |
| 2009/0318949 A1 | 12/2009 | Ganpath et al. | |
| 2009/0319029 A1 | 12/2009 | Evans et al. | |
| 2010/0004728 A1 | 1/2010 | Rao et al. | |
| 2010/0036360 A1 | 2/2010 | Herbowy et al. | |
| 2010/0106087 A1 | 4/2010 | Evans et al. | |
| 2010/0114291 A1* | 5/2010 | Kolbel | A61F 2/07 623/1.12 |
| 2010/0131040 A1 | 5/2010 | Robin | |
| 2010/0280588 A1 | 11/2010 | Schreck | |
| 2012/0022573 A1* | 1/2012 | Kratzberg | A61B 17/12022 606/194 |
| 2012/0116427 A1* | 5/2012 | Raza | A61B 17/1155 606/153 |
| 2012/0197284 A1* | 8/2012 | Ogle | A61B 17/12036 606/195 |
| 2012/0203264 A1* | 8/2012 | Karwa | A61B 17/12118 606/194 |
| 2015/0127029 A1* | 5/2015 | Raza | A61B 17/1155 606/153 |

FOREIGN PATENT DOCUMENTS

| | | |
|---|---|---|
| DE | 295 21 548 U1 | 2/1995 |
| DE | 295 21 776 U1 | 2/1995 |
| EP | 0 177 330 B1 | 6/1991 |
| EP | 0 596 145 A1 | 5/1994 |
| EP | 0 621 015 B1 | 10/1994 |
| EP | 0 659 389 A1 | 6/1995 |
| EP | 0 688 545 B1 | 12/1995 |
| EP | 0 689 806 A1 | 1/1996 |
| EP | 0 712 614 A1 | 5/1996 |
| EP | 0 740 928 B1 | 11/1996 |
| EP | 0 747 020 A2 | 12/1996 |
| EP | 0 775 470 A1 | 5/1997 |
| EP | 0 782 841 B1 | 7/1997 |
| EP | 0 783 873 B1 | 7/1997 |
| EP | 0 783 874 B1 | 7/1997 |
| EP | 0 762 856 B1 | 9/1998 |
| EP | 0 880 948 A1 | 12/1998 |
| EP | 0 904 745 A2 | 3/1999 |
| EP | 0 974 314 A2 | 1/2000 |
| EP | 0 732 088 B1 | 4/2000 |
| EP | 0 846 450 B1 | 12/2001 |
| EP | 0 846 449 B1 | 1/2002 |
| EP | 0 846 452 B1 | 1/2002 |
| EP | 1 433 438 | 6/2004 |
| EP | 1 181 901 B1 | 11/2005 |
| EP | 1 110 515 B1 | 3/2006 |
| EP | 0 828 461 B2 | 7/2006 |
| EP | 1 181 902 B2 | 3/2009 |
| ES | 1 038 606 | 7/1998 |
| FR | 2834199 A1 | 7/2003 |
| JP | 04-25755 | 1/1992 |
| JP | 08-336597 | 12/1996 |
| JP | 9-511160 | 11/1997 |
| JP | 2000-500047 | 1/2000 |
| WO | WO 93/13825 | 7/1993 |
| WO | WO 94/24961 | 11/1994 |
| WO | WO 95/21592 | 8/1995 |
| WO | WO 96/34580 | 11/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/19652 | 6/1997 |
| WO | WO 97/26936 | 7/1997 |
| WO | WO 97/29716 | 8/1997 |
| WO | WO 97/33532 | 9/1997 |
| WO | WO 97/45072 | 12/1997 |
| WO | WO 98/02100 | 1/1998 |
| WO | WO 98/53761 | 12/1998 |
| WO | WO 99/29262 | 6/1999 |
| WO | WO 99/44536 | 9/1999 |
| WO | WO 99/47077 | 9/1999 |
| WO | WO 99/58084 | 11/1999 |
| WO | WO 00/51522 | 9/2000 |
| WO | WO 01/21108 | 3/2001 |
| WO | WO 01/66038 A2 | 9/2001 |
| WO | WO 02/102282 | 12/2002 |
| WO | WO 2004/045393 A2 | 6/2004 |
| WO | WO 2005/037076 | 4/2005 |

OTHER PUBLICATIONS

Gilling-Smith, "Stent Graft Migration After Endovascular Aneurysm Repair," presented at 25th International Charing Cross Symposium, Apr. 13, 2003 [Power Point Presentation and Transcript], 56 pages total.

International Search Report and the Written Opinion of the International Searching Authority, mailed Feb. 23, 2012, regarding International Application No. PCT/US2011/061061 filed Nov. 16, 2011.

International Search Report and Written Opinion of PCT Application No. PCT/US2006/062257, mailed Jan. 18, 2008, 7 pages total.

US 6,413,270, 07/2002, Thornton et al. (withdrawn)

* cited by examiner

DEVICES AND METHODS TO TREAT VASCULAR DISSECTIONS

PRIORITY INFORMATION AND INCORPORATION BY REFERENCE

This application is a United States national stage application under 35 U.S.C. §371 of PCT Application No. PCT/US2011/061061 designating the United States, filed on Nov. 16, 2011, which claims priority benefit under 35 U.S.C. §119 (e) of U.S. Provisional Application 61/414,819 filed Nov. 17, 2010, which application is hereby incorporated by reference as if fully set forth herein.

BACKGROUND OF THE DISCLOSURE

1. Field of the Invention

The present disclosure relates to methods and devices for the treatment of aortic dissections.

2. Background of the Disclosure

An aortic dissection is a dangerous condition with a high mortality rates. In an aortic dissection, a tear typically develops in the intima of the aorta that propagates along the vessel wall delaminating the inner layer of the aorta from the outer layer. Blood enters the space between the layers creating a false lumen. Several additional tears or entry points can be created between true lumen of the aorta and the false lumen. In the acute phase, dissections may close off perfusion from the aorta to vital organs. In the chronic phase, the weakened tissue can develop into aneurysm and ultimately rupture. Dissections involving the ascending aorta are referred to as Type A dissections. Dissections only involving the descending aorta are referred to as Type B dissections.

Current treatments for dissections include medical management to lower the blood pressure of the patient and reduce the hemodynamic stresses on the diseased vessel. If dissections are symptomatic, surgical intervention is necessary. Portions of the diseased aorta are replaced by a surgical graft and the dissection flap is reattached. More recently, stent grafts have been used to close the primary entry point into the false lumen with the goal to thrombose the false lumen and maintain patency of the true lumen.

Endovascular treatment of aortic dissections in the thoracic aorta using a stent graft may risk inter-operative and post-operative complications. Catheter delivery systems of thoracic stent grafts typically have a profile of 20-24Fr requiring a cut-down or conduit for delivery. Vessel damage by the large delivery catheters used is common. Stent grafts are difficult to deploy accurately in the thoracic aorta due to high blood flow. Often only the primary entry point of a dissection is covered by the stent graft allowing continuous pressurization of the false lumen through secondary entry points. Long term, a pressurized false lumen tends to expand and become aneurismal. Coverage of all entry points along the dissection by stent grafts contains the risk of local ischemia or paraplegia due to obstruction of vital branch vessels.

There is a clear need for an improved method to treat aortic dissections. The current application provides novel solutions to the treatment of aortic dissections.

SUMMARY OF SOME EMBODIMENTS

Some embodiments disclosed herein relate to a device for treating aortic dissections having a false lumen comprising a support structure in a true lumen of the aorta and an inflatable structure in the false lumen. In some embodiments, the support structure can be in a compressed state during the delivery in the aorta. The support structure can be expanded to approximately the diameter of the true lumen when placed in the true lumen. The inflatable structure can be in a collapsed state during the delivery in the false lumen and inflated to displace the blood in the false lumen.

Some embodiments disclosed herein relate to a device for redirecting flow between at least two blood lumen in the body comprising a support structure in the first lumen and an inflatable structure in a second lumen. In some embodiments, the support structure can be in a compressed first state during the delivery into a first lumen. The support structure can be expandable to a second state to maintain blood flow through the first lumen. The inflatable structure can be in a collapsed state during the delivery into a second lumen and inflated to a second state to block blood flow through the second lumen.

Some embodiments disclosed herein relate to a method of treating an aortic dissection comprising placing a support structure in the true lumen to maintain the patency of the true lumen, placing an inflatable structure into the false lumen, and inflating the inflatable structure to displace the blood in the false lumen.

Some embodiments disclosed herein relate to a method of redirecting blood flow between two lumens in the body comprising placement of a implantable support structure in a first lumen to maintain blood flow through the first lumen and placement of an implantable inflatable structure into a second lumen and inflating the inflatable structure to block blood flow through the second lumen.

Some embodiments disclosed herein comprise a device and method for the treatment of aortic dissections comprising placing a stent in the true lumen and displacing the blood in the false lumen with an inflatable bag. The device can have a support structure for supporting a true lumen of an aorta and an inflatable structure to be positioned in the false lumen. The support structure can be supported in a compressed state when the device is in a pre-deployment state and during delivery to the true lumen, and can be expanded in the aorta during deployment to approximately the diameter of the true lumen. The inflatable structure can be supported in a compressed state when the device is in a pre-deployment state and during advancement of the inflatable structure into the false lumen, and can be inflated in the false lumen to displace the blood in the false lumen.

Some embodiments disclosed herein comprise a device for treating aortic dissections having a false lumen, comprising a support structure to be positioned in a true lumen of the aorta to support the true lumen when the support structure is deployed, and an inflatable structure for positioning in the false lumen. The support structure can be supported in a compressed state when the device is in a pre-deployment state and during delivery to the true lumen and expandable in the aorta to the approximate diameter of the true lumen. The inflatable structure can be supported in a compressed state when the device is in a pre-deployment state and during advancement into the false lumen and inflatable in the false lumen to displace the blood in the false lumen.

Some embodiments disclosed herein comprise a device for altering blood flow in the body, comprising a support structure to be deployed in a first body lumen, and an inflatable structure to be deployed in a second body lumen. In some embodiments, the support structure can be in a compressed first state during delivery into the first lumen and expanded to a second state in the first lumen to maintain blood flow through the first lumen. The inflatable structure can be in a collapsed state during delivery into the second lumen and after being advanced into the second lumen be inflated to a second state in the second lumen to block blood flow through the second lumen. In some embodiments, the second lumen is adjacent to the first lumen.

Some arrangements disclosed herein comprise a method of treating an aortic dissection having a true lumen and a false lumen, comprising deploying a support structure in the true lumen of a blood vessel adjacent to or overlapping a portion of the dissection to maintain the true lumen in an open state, advancing an inflatable structure in a collapsed state into the false lumen, and inflating the inflatable structure to displace the blood in the false lumen.

Some arrangements disclosed herein comprise a method of redirecting blood flow between two lumens in the body, comprising positioning an implantable support structure in a first lumen to maintain blood flow through the first lumen, and positioning an implantable inflatable structure into a second lumen and inflating the inflatable structure to block blood flow through the second lumen.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to be limiting. The following are brief descriptions of the drawings, which may not be drawn to scale.

DETAILED DESCRIPTION

This disclosure relates to a novel devices and methods for treating aortic dissections. Specifically, methods and devices are disclosed herein that are appropriate for the treatment of acute Type B dissections involving the descending aorta. However, some embodiments and/or components of the devices and methods disclosed herein have applications to treat other vascular defects or diseases and all such uses are contemplated as being part of this disclosure.

Some embodiments of the proposed devices or treatment are configured to obliterate the false lumen while maintaining patency of the true lumen. This can be accomplished by placement of a stent in the true lumen to reestablish the original flow lumen of the aorta. The false lumen can be filled with an inflatable bag that displaces the blood in the false lumen and prevents further pressurization of the aortic wall in the false lumen.

Figure 1:
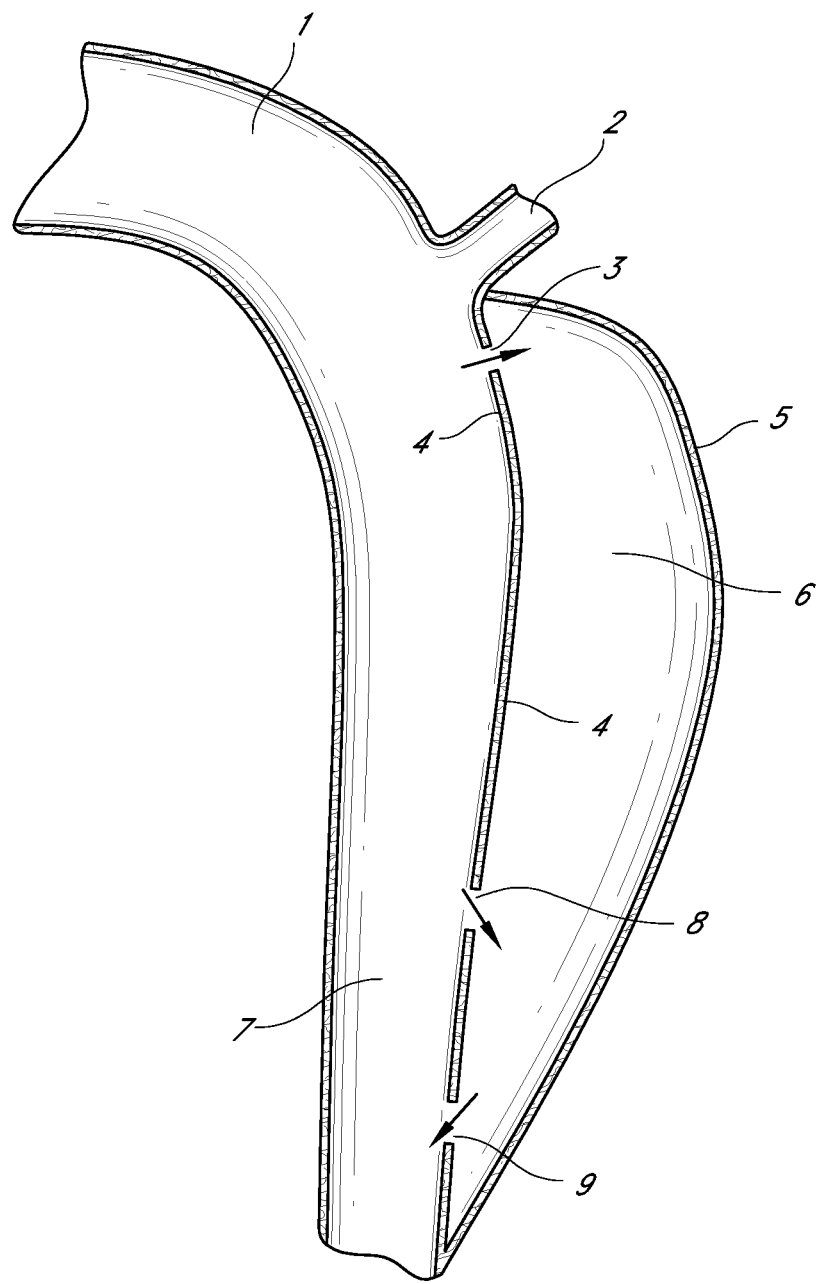
FIG. 1 illustrates one non-limiting example of an aortic dissections.

FIG. 1 illustrates a non-limiting example of a type B dissection in the human aorta. A tear 3 in the inner layer of the aorta 1 distal to the subclavian artery 2 typically allows blood to enter into the aortic wall (see arrows) and separate or peel the inner layer 4 of the aorta from the outer layer 5. The space created by the blood between the two layers is referred to as the false lumen 6. The tear 3 is referred as the primary entry point into the false lumen. The separated inner layer 4 is referred to as the flap. The portion of the aorta within the inner layer of the aorta along the dissection is referred to as the true lumen 7. In some cases, multiple entry and exit openings may exist along the flap, as indicated by the openings 8 and 9.

Figure 2:
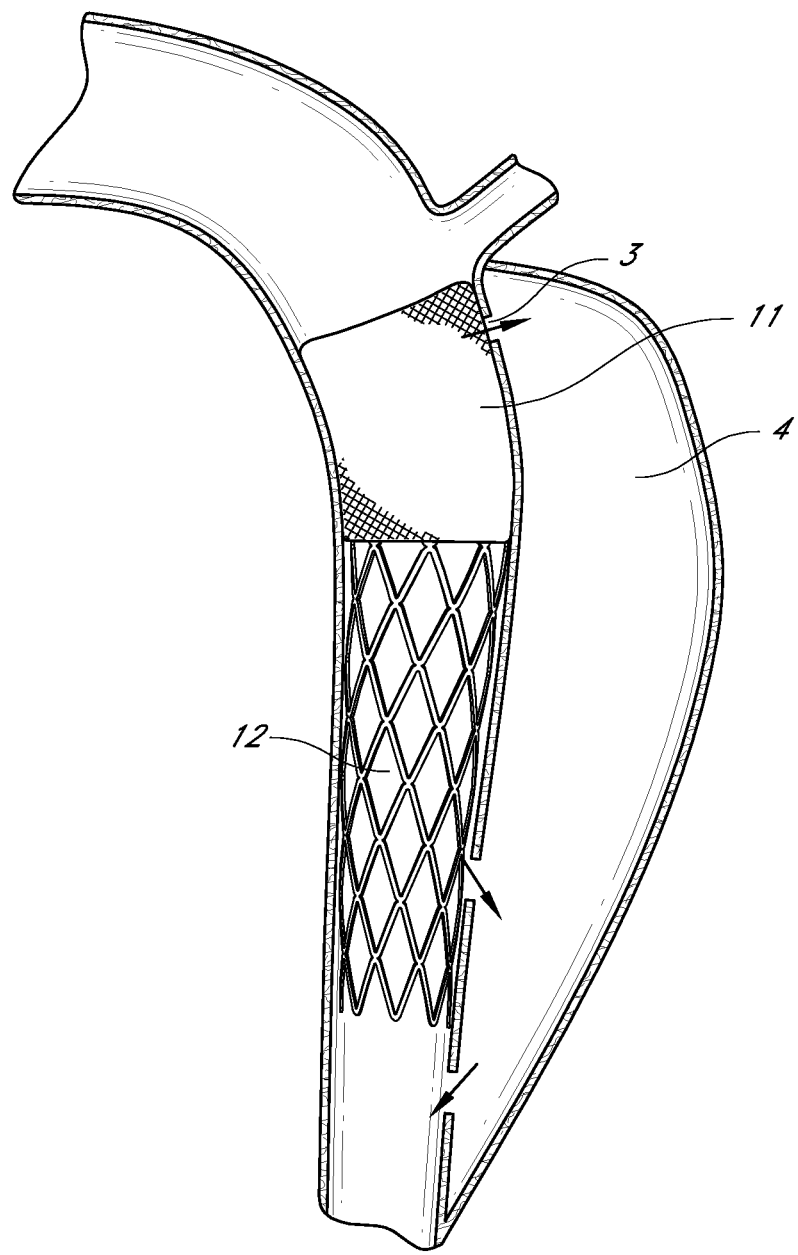
FIG. 2 illustrates treatment of an aortic dissection with a stent and a stent graft of the prior art.

FIG. 2 show devices used in a current method for treating type B dissections. A covered stent 11 is placed at the location of the primary entry point to prevent blood from entering the false lumen through the primary entry point. A bare stent 12 is placed in the true lumen distal to the covered stent 11 to prevent the flap from obstructing the true lumen.

Figure 3:
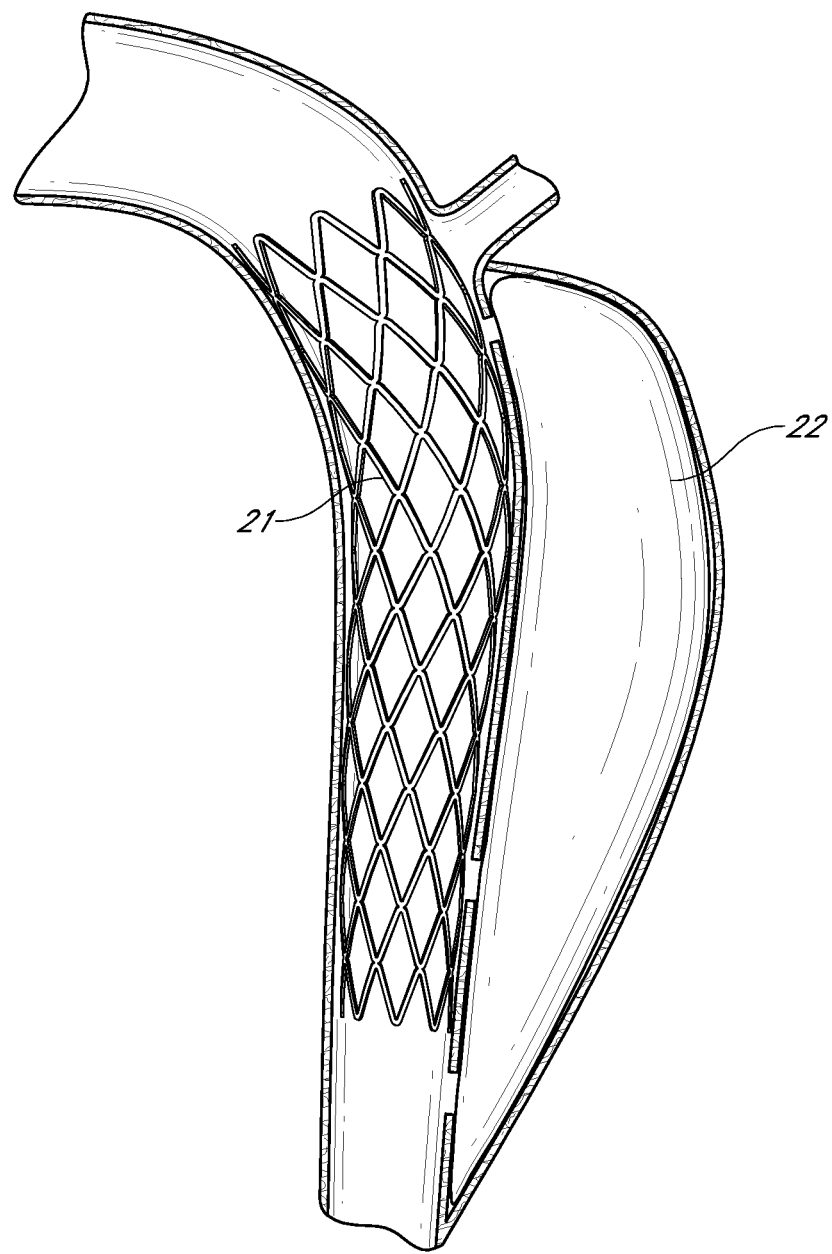
FIG. 3 illustrates an embodiment of a device system configured to treat dissections

FIG. 3 shows an embodiment of the proposed device. A support structure 21 such as a balloon expandable stent or a self-expandable stent is placed in the true lumen to maintain patency of the true lumen. An inflatable structure 22 is placed in the false lumen such that, in the inflated state, it displaces the blood in the false lumen. By displacing the blood in the false lumen, the effect of blood pressure on the wall of the false lumen can be reduced or eliminated and further dilation of the false lumen can be prevented or inhibited.

The support structure in the true lumen can comprise a single stent or multiple stents. In the case of multiple stents, the stents can be positioned adjacent to one another, spaced apart or can be positioned relative to one another so as to at least partially overlap. The stents can be flexible so as to conform to the curvature of the aorta. Some embodiments of the stents can have large spaces between the struts to allow for flow into branch vessels of the aorta.

Figure 4:
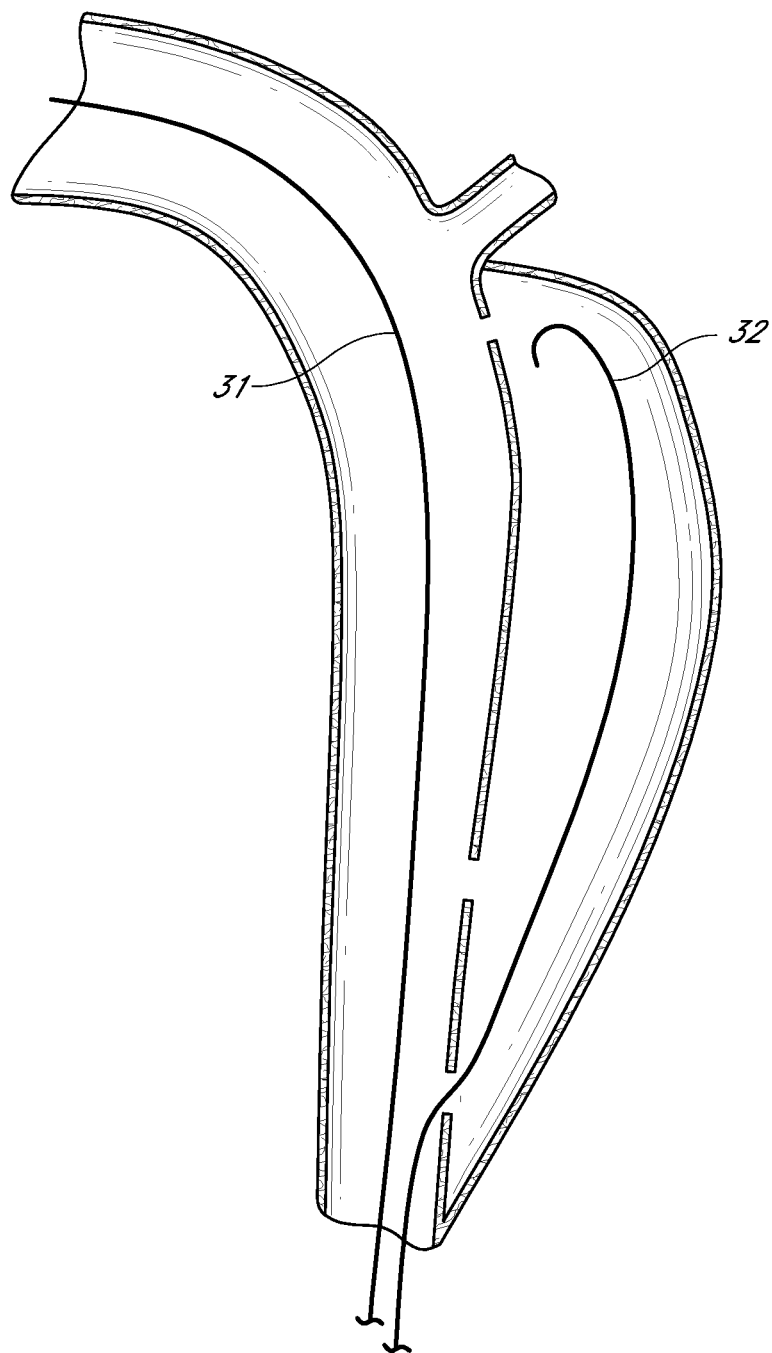
FIG. 4 illustrates the advancement of guidewires into the diseased portion of a blood vessel.
Figure 5:
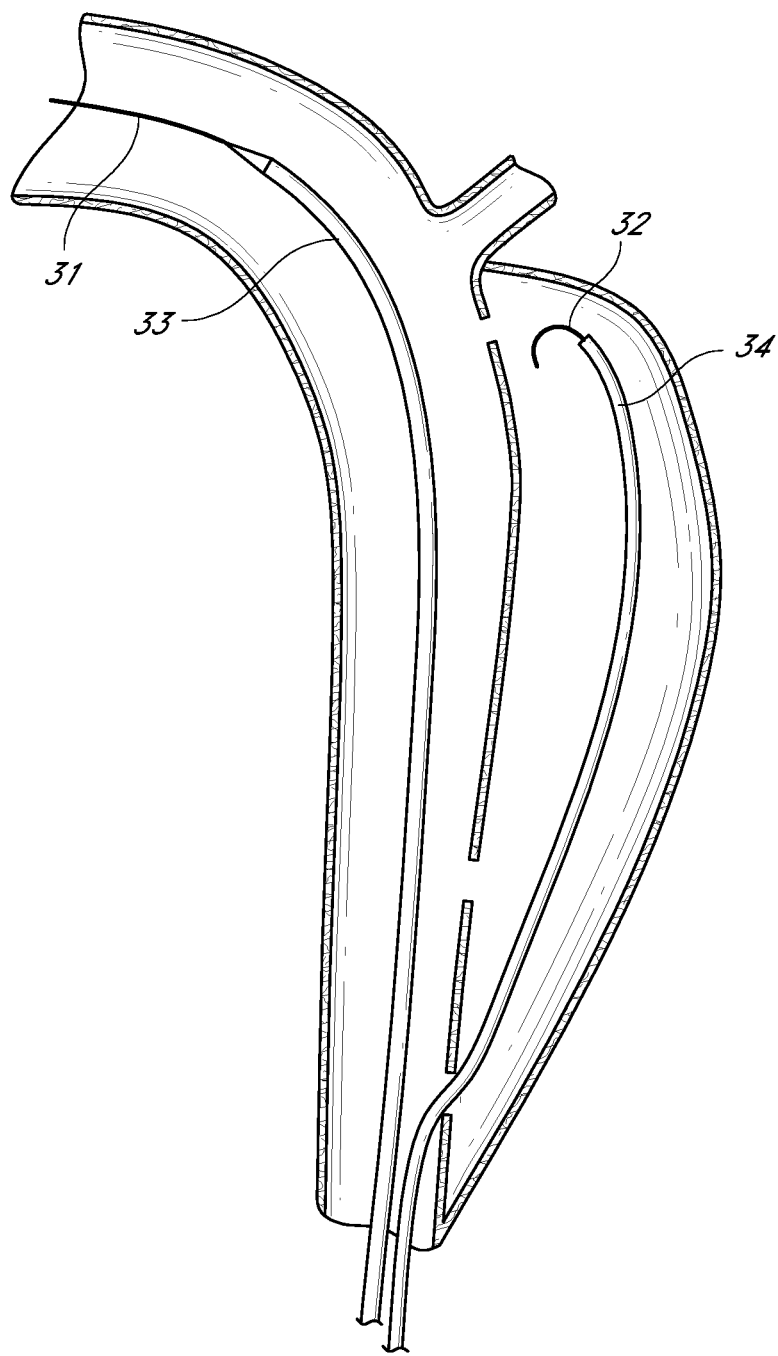
FIG. 5 illustrates the advancement catheters over the guidewires.
Figure 6:
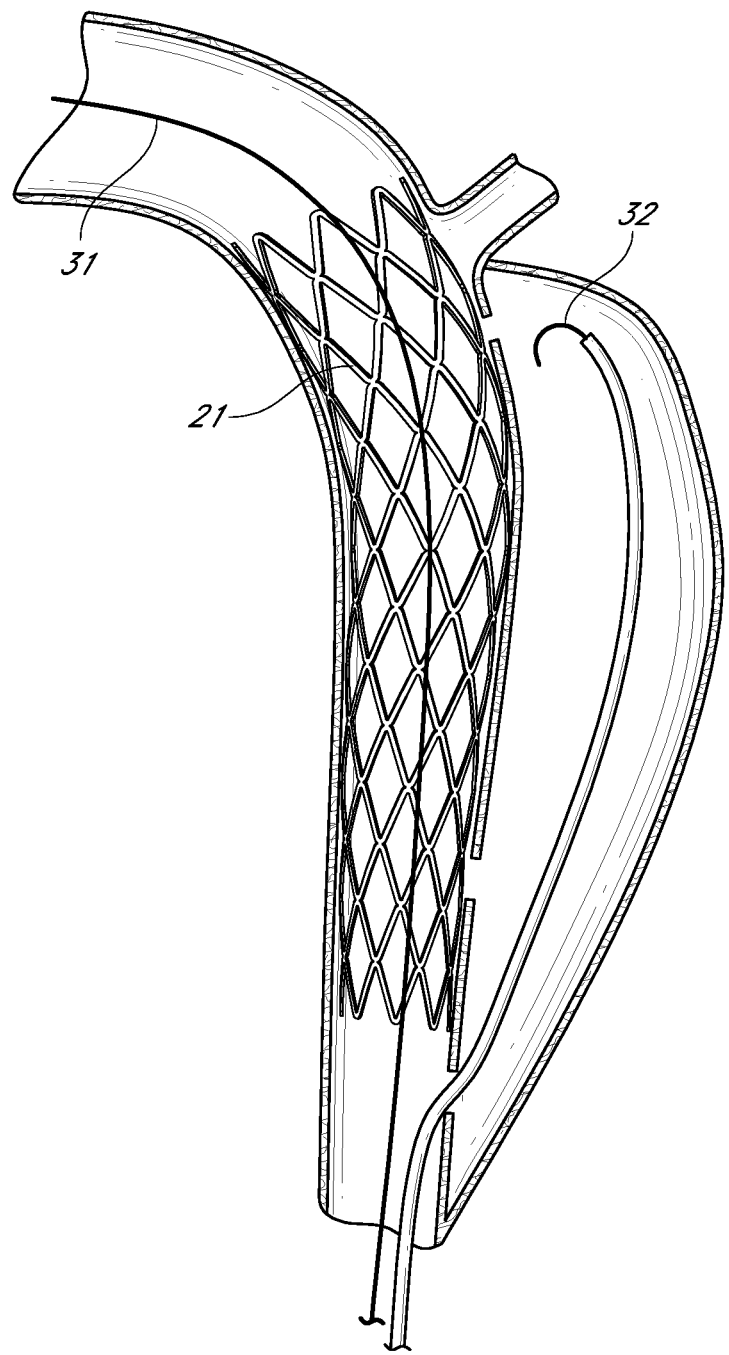
FIG. 6 illustrates a support structure deployed in the true lumen.
Figure 7:
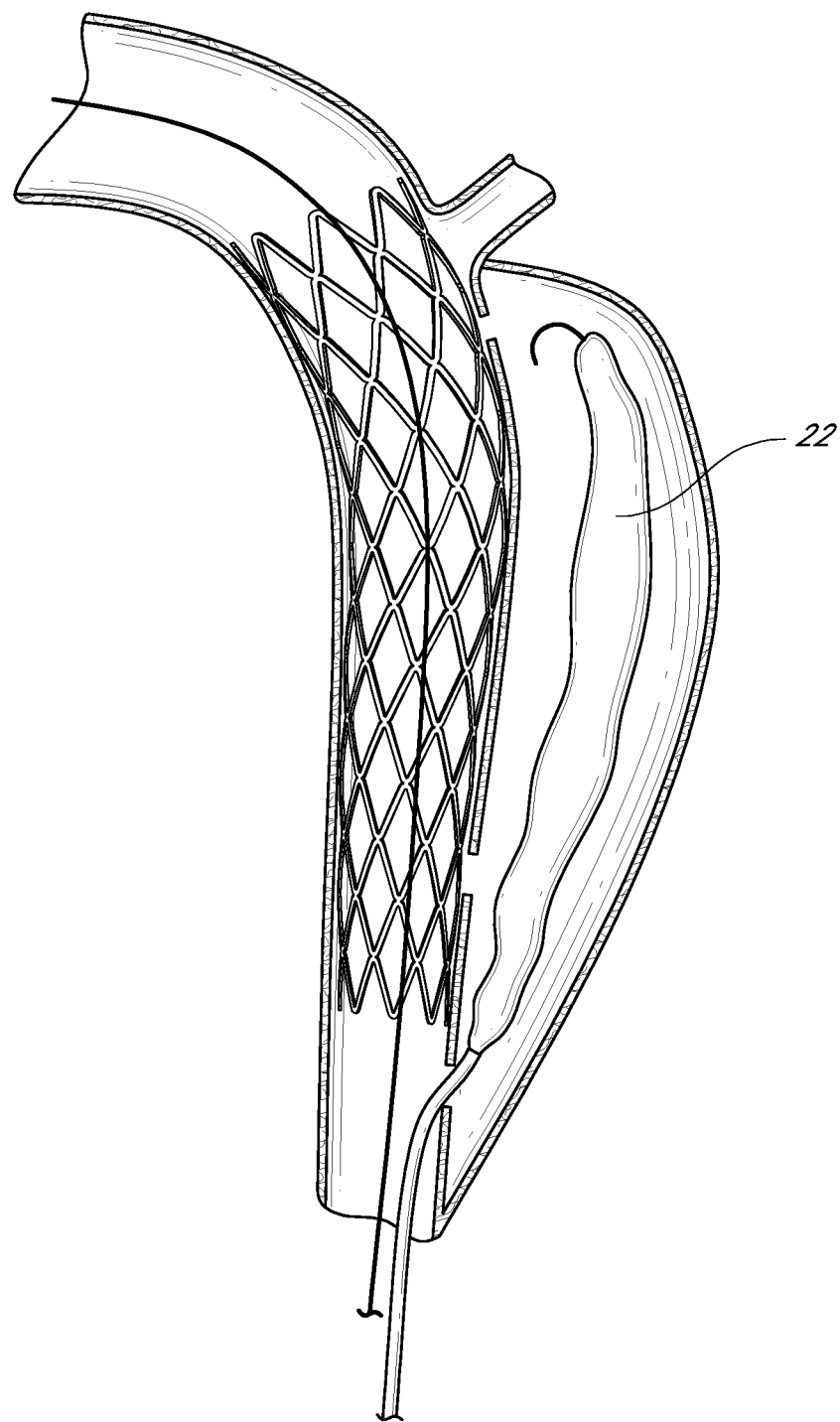
FIG. 7 illustrates a support structure in a state of being partially deployed in the false lumen.
Figure 8:
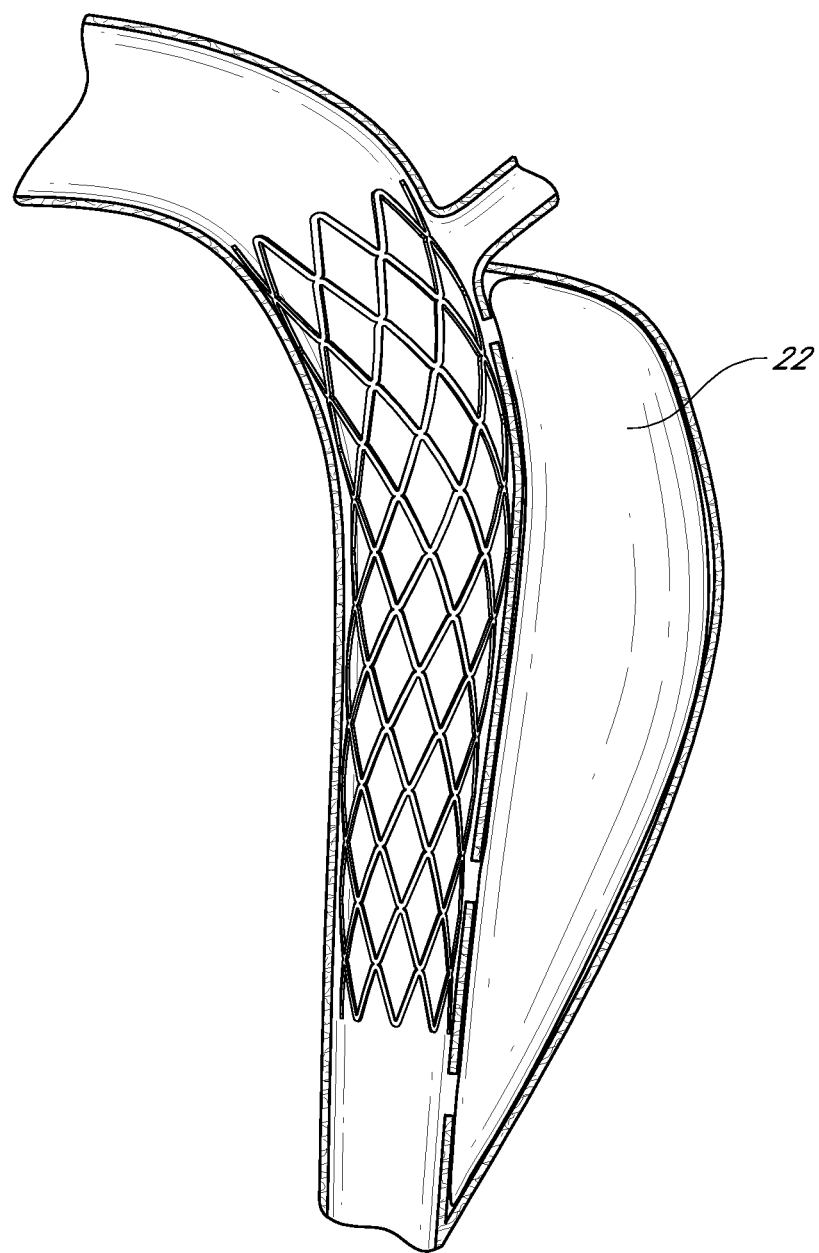
FIG. 8 illustrates support structure of FIG. 7 fully inflated to act as the support structure in the false lumen.

FIGS. 4-8 illustrate the steps of a method of treating a dissection with a device system as described herein. The order of the steps described below can be altered or adjusted, and some of the steps can be omitted or combined with other steps. For example, a support structure can be deployed in the false lumen before a support structure is deployed in the true lumen, or vice versa. FIG. 4 illustrates the advancement of two guidewires from the femoral artery into the aorta. A first guidewire 31 is located in the true lumen and a second guidewire 32 is placed into the false lumen. FIG. 5 illustrates a catheter 33 comprising a support structure 21 having been inserted over the first guidewire 31 into the true lumen, and a catheter 34 comprising an inflatable structure 22 having been inserted into the false lumen. In the next step, the support structure is deployed in the true lumen. FIG. 6 illustrates the support structure (a stent) 21 deployed in the true lumen and the first catheter retracted. With reference to FIG. 7, the inflatable structure 22 is shown unsheathed (partially deployed). FIG. 7 illustrates the unsheathed inflatable (support) structure 22. As illustrated in FIG. 8, the inflatable structure 22 has been inflated to displace the blood in the false lumen.

Figure 9:
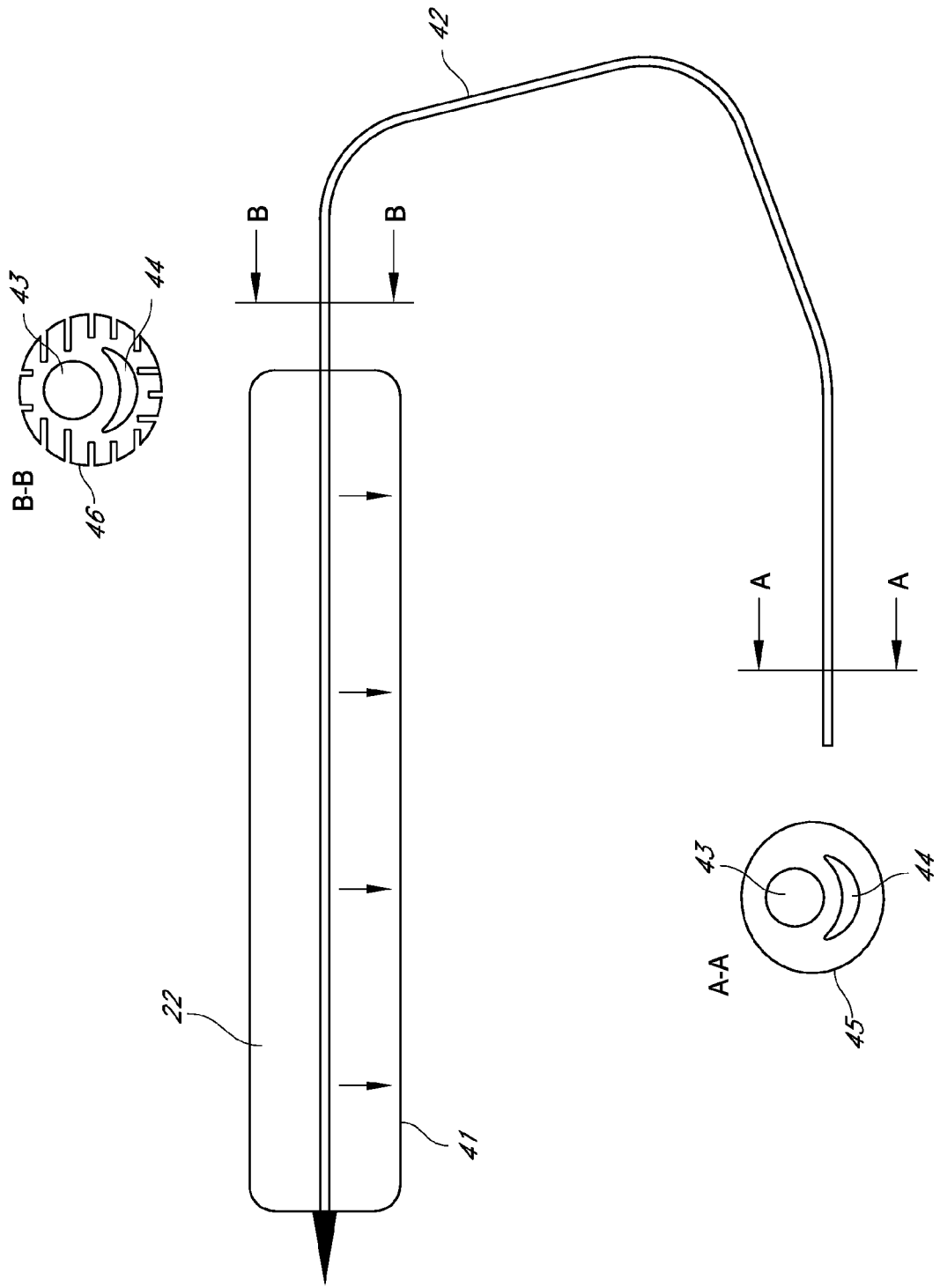
FIG. 9 illustrates details of an inflatable support structure.

FIG. 9 shows an embodiment of the inflatable structure 22. The inflatable structure 22 can comprise a bag 41, a catheter 42 with a guidewire lumen 43, and a fill lumen 44. Openings along the catheter 42 can allow inflation medium to pass from the fill lumen 44 into the bag 41. Section A-A illustrates a first cross-section 45 of the catheter 42 comprising the guidewire lumen 43 and the fill lumen 44. Section B-B illustrates a second cross-section 46 of the catheter 42 comprising the guidewire lumen 43 and the fill lumen 44. The second cross-section 46 can be located proximal to the bag 41. The catheter shaft as shown in cross-section 46 can be weakened or otherwise configured to be predictably frangible to allow for breaking and detachment of the catheter 42 at approximately the location of the second cross-section 46 on the catheter and removal of the distal portion of the catheter 42 from the body of the patient.

There are many suitable methods of or embodiments filling the inflatable structure. Several potential embodiments are discussed here for illustration purposes. In some embodiments, the bag can be porous to allow blood to enter the interior of the bag. Hydrogel can be inserted into the bag through the fill lumen. The hydrogel can be delivered in form of spheres, tubes, or pellets. In some embodiments, when the hydrogel enters the bag, the hydrophilic properties of the bag can draw blood through the porous wall into the bag. The hydrogel can absorb the blood and swell. The swelling hydrogel can cause the bag to inflate. Hydrogel can be inserted into the bag until the inflated bag fills the false lumen. The swell pressure in the bag can be equal or higher than the blood pressure. The stagnant blood in the hydrogel can coagulate, causing the false lumen to thrombose. Contrast medium can be added to the hydrogel during filling to visualize the expanding bag under fluoroscopy.

In some embodiments, the bag can be impermeable. Blood can be extracted from the patient and a thrombolytic agent can be added to the blood. The mixture can be injected into the bag to inflate the bag. Additionally, a polymeric solution comprising a polymer and a cross-linking agent can be injected through the fill lumen into the bag. The polymer cross-links after injection. Alternatively, the hydrogel can be a thermosensitive sol-gel reversible hydrogel. The hydrogel can be configured such that, below body temperature, the hydrogel is in a liquid state. This can facilitate injection of the hydrogel into the inflatable structure. When the hydrogel warms up to body temperature, it can undergo a phase transition and become more rigid or become a solid.

It will obvious to the reader skilled in the art that many materials can be used to fill the bag. Preferably, the fill medium is biocompatible. As mentioned, in some embodiments, the fill medium can be configured to be liquid during the injection phase and to solidify after injection.

The bag can be made from various thin-wall materials including but not limited to ePTFE, polyurethane, and woven and knitted polyester or silk. The wall can have a thickness between 0.0001 in (or approximately 0.0001 in) and 0.01 in (or approximately 0.01 in) or between 0.001 in (or approximately 0.001 in) and 0.004 in (or approximately 0.004 in). The bag can be made from a material that is strong enough to avoid rupture of the bag during inflation. In some embodiments, the bag can be inflated to a pressure in excess of the systolic blood pressure to completely displace the blood from the false lumen. The bag can be configured such that the burst pressure of the bag is higher than the difference between the systolic and diastolic blood pressure. If the wall of the bag is porous to allow for blood to enter the bag, the pore size can be larger than the size of a blood cell. The pores can be larger than 6 micrometers (or approximately 6 micrometers) and smaller than the size of the hydrogel pellets. The pore size can be between 10 micrometers (or approximately 10 micrometers) and 1 millimeter (or approximately 1 millimeter). In arrangements in which liquid medium is injected through the fill lumen into the bag, the wall of the bag can be configured to be impermeable to the fill medium during injection and during solidification of the medium. The entry pressure needed to pass the fill medium through the wall of the bag can be larger than 50 mmHg (or approximately 50 mmHg). In some embodiments, the entry pressure can be larger than 200 mmHg (or approximately 200 mmHg).

In some embodiments, the delivery system and the fill lumen to the bag can be detached from the bag and retracted from the patient once the bag is filled. In some embodiments, the bag can have a one-way valve that prevents fill medium from escaping from the bag once the fill tube is detached.

The filling of the bag can be monitored under fluoroscopy. Additionally, radiopaque markers can be attached to the bag to visualize the size of the bag during inflation. In some embodiments, contrast medium can be injected into the bag to visualize the size of the bag. The contrast medium can be injection into the false lumen to visualize the blood being displaced by the bag. In some embodiments, the inflation of the bag can be monitored by measuring the pressure in the bag. A pressure sensor can be placed in the bag. Alternatively or additionally, the pressure in the fill lumen can be monitored. In some arrangements, a second lumen can be connected to the bag and the pressure in the second lumen can be monitored. Further, in some arrangements, the pressure in the aorta and the bag can be measured and the differential pressure between the aortic pressure and the bag pressure can be displayed.

As mentioned earlier, the stent in the true lumen can be partially covered with a graft. The graft can cover the primary entry point into the false lumen to reduce the blood pressure in the false lumen. This can reduce the force that the flap exerts on the stent in the true lumen. Alternatively, an aortic balloon can be placed at or proximal to the primary entry point during filling of the bag to block blood from entering the false lumen. To prevent the stent from collapsing during filling of the bag, a balloon can be placed inside the stent and inflated to support the stent.

The support structure and the inflatable structure can be delivered to the treatment site through the leg arteries of the patient or other branch vessels of the aorta including but not limited to the head arteries and the arm arteries. Alternatively, the devices can be delivered through surgical incisions into the aorta. For example, access to the thoracic aorta can be obtained by an incision into the ascending aorta or the aortic arch. In an alternative approach, access to the aorta may be gained through the apex of the heart or from the right heart. This approach may be preferred in case of Type A dissections that originate in the ascending aorta. It will obvious to those skilled in the art that any combinations of the above approaches can be used to deliver and deploy the support structure into the true lumen and the inflatable structure in the false lumen.

In some dissections, vital organs can be perfused by the false lumen and not the true lumen. In this case, it may be preferred to place the support structure in the false lumen and the inflatable structure in the true lumen. It will obvious to those skilled in the art that the combination of a support structure and an inflatable structure can be used to redirect flow between any of two parallel blood or air lumens in the body.

As will be recognized, certain embodiments described herein can be embodied within a form that does not provide all of the features and benefits set forth herein, as some features can be used or practiced separately from others. Unless otherwise defined herein, the term approximate or approximately means values within 10% of the stated value.

Although this disclosure has been described in the context of exemplifying embodiments and examples, it will be understood by those skilled in the art that the embodiments disclosed herein extend beyond the specifically disclosed embodiments to other alternative embodiments and obvious modifications and equivalents thereof. In addition, while a number of variations have been shown and described in detail, other modifications, which are within the scope of this disclosure, will be readily apparent to those of skill in the art based upon this disclosure. It can be also contemplated that various combinations or subcombinations of the specific features and aspects of the embodiments can be made and still fall within the scope of the invention. Accordingly, it should be understood that various features and aspects of the disclosed embodiments can be combine with or substituted for one another in order to form varying modes of treatment as described herein. Thus, it is intended that the scope of that herein disclosed should not be limited by the particular disclosed embodiments described above.

What is claimed is:

1. A method of treating an aortic dissection having a true lumen and a false lumen, comprising:
   deploying a support structure in the true lumen of a blood vessel adjacent to or overlapping a portion of the dissection to maintain the true lumen in an open state;
   advancing a bag in a collapsed state as part of a catheter with a fill lumen into the false lumen;
   inflating the bag while said bag is in the false lumen using a filling medium provided to said bag through the fill lumen such that the bag conforms to an inner layer between the true lumen and the false lumen and covers a tear formed in the inner layer to block blood flow through the false lumen; and
   separating the bag from the catheter while maintaining the bag in the false lumen.

2. The method of claim 1, wherein the support structure is a balloon expandable stent or a self-expandable stent.

3. The method of claim 1, comprising sealing at least one opening into the dissection with a support structure that is partially covered with a graft.

4. The method of claim 1, comprising inflating the bag with the filling medium comprising a polymer or monomer that crosslinks after injection.

5. The method of claim 4, wherein the polymer comprises polyethylene glycol.

6. The method of claim 1, wherein the bag is made from ePTFE, polyurethane, Dacron, woven or knitted biocompatible fibers, or other thin-wall biocompatible material.

7. The method of claim 1, wherein the bag comprises an embolization agent.

8. The method of claim 1, further comprising monitoring a pressure in the bag during inflation.

9. The method of claim 1, wherein the filling medium for inflating the bag is liquid during injection and changes phase to a solid after injection.

10. The method of claim 1, comprising inflating the bag to displace the blood in the false lumen after deploying the support structure in the true lumen of the blood vessel adjacent to or overlapping a portion of the dissection.

11. The method of claim 1, further comprising advancing the bag into the false lumen through an opening closer to a downstream end of the false lumen than an upstream end of the false lumen.

12. The method of claim 1, wherein inflating the bag comprises inflating the bag to a pressure in excess of systolic blood pressure.

* * * * *